United States Patent
Foley et al.

(10) Patent No.: US 8,366,695 B2
(45) Date of Patent: Feb. 5, 2013

(54) ADAPTOR FOR OSTOMY COUPLING

(75) Inventors: Theodore Foley, East Brunswick, NJ (US); Kenneth Johnsen, Piscataway, NJ (US); Gary Oberholtzer, Feasterville, PA (US); Nino Pionati, Washington Crossing, PA (US)

(73) Assignee: ConvaTec Technologies, Inc., Las Vegas, NV (US)

( * ) Notice: Subject to any disclaimer, the term of this patent is extended or adjusted under 35 U.S.C. 154(b) by 542 days.

(21) Appl. No.: 12/673,665

(22) PCT Filed: Aug. 18, 2008

(86) PCT No.: PCT/US2008/073492
§ 371 (c)(1),
(2), (4) Date: Feb. 16, 2010

(87) PCT Pub. No.: WO2009/023870
PCT Pub. Date: Aug. 18, 2008

(65) Prior Publication Data
US 2011/0071485 A1    Mar. 24, 2011

Related U.S. Application Data

(60) Provisional application No. 60/956,233, filed on Aug. 16, 2007.

(51) Int. Cl.
*A61F 5/44* (2006.01)

(52) U.S. Cl. ........ 604/342; 604/344; 604/338; 604/332; 604/339; 604/341; 604/343; 604/336

(58) Field of Classification Search .................. 604/342, 604/344, 338, 332, 339, 341, 343, 336
See application file for complete search history.

(56) References Cited

U.S. PATENT DOCUMENTS

| 4,419,100 A | 12/1983 | Alexander |
| 4,610,676 A | 9/1986 | Schneider et al. |
| 4,610,677 A | 9/1986 | Mohiuddin |
| 4,786,285 A * | 11/1988 | Jambor .................. 604/342 |
| 5,730,735 A | 3/1998 | Holmberg et al. |
| 5,957,905 A | 9/1999 | Steer |
| 2007/0088300 A1 | 4/2007 | Cline |
| 2007/0129695 A1 | 6/2007 | Blum |

FOREIGN PATENT DOCUMENTS

| GB | 1571657 | 11/1977 |
| WO | WO2005070356 A1 | 8/2005 |
| WO | WO2009/023871 | 2/2009 |

* cited by examiner

*Primary Examiner* — Tatyana Zalukaeva
*Assistant Examiner* — Ginger T Chapman
(74) *Attorney, Agent, or Firm* — Stuart E. Krieger (57) ABSTRACT

An adapter is disclosed for an ostomy coupling. The adapter provides a floatable coupling characteristic to an ostomy body fitment that has a non-floatable coupling part. The adapter comprises a first coupling part for attaching to the non-floating coupling part of the body fitment, a second coupling part for releasably attaching to an ostomy appliance, and a flexible collar between the first and second coupling parts. The flexible collar permits the second coupling part to be displaced away from the first coupling part, thereby creating a space for an ostomate to manually brace the second coupling part against an attachment force when an appliance is fitted.

24 Claims, 6 Drawing Sheets

ADAPTOR FOR OSTOMY COUPLING

FIELD OF THE INVENTION

The present invention relates to an ostomy coupling for removably attaching an ostomy appliance to a body fitment worn on the body of an ostomate. In one form, the invention relates to providing a body fitment with a floatable coupling part.

BACKGROUND TO THE INVENTION

Figure 1:
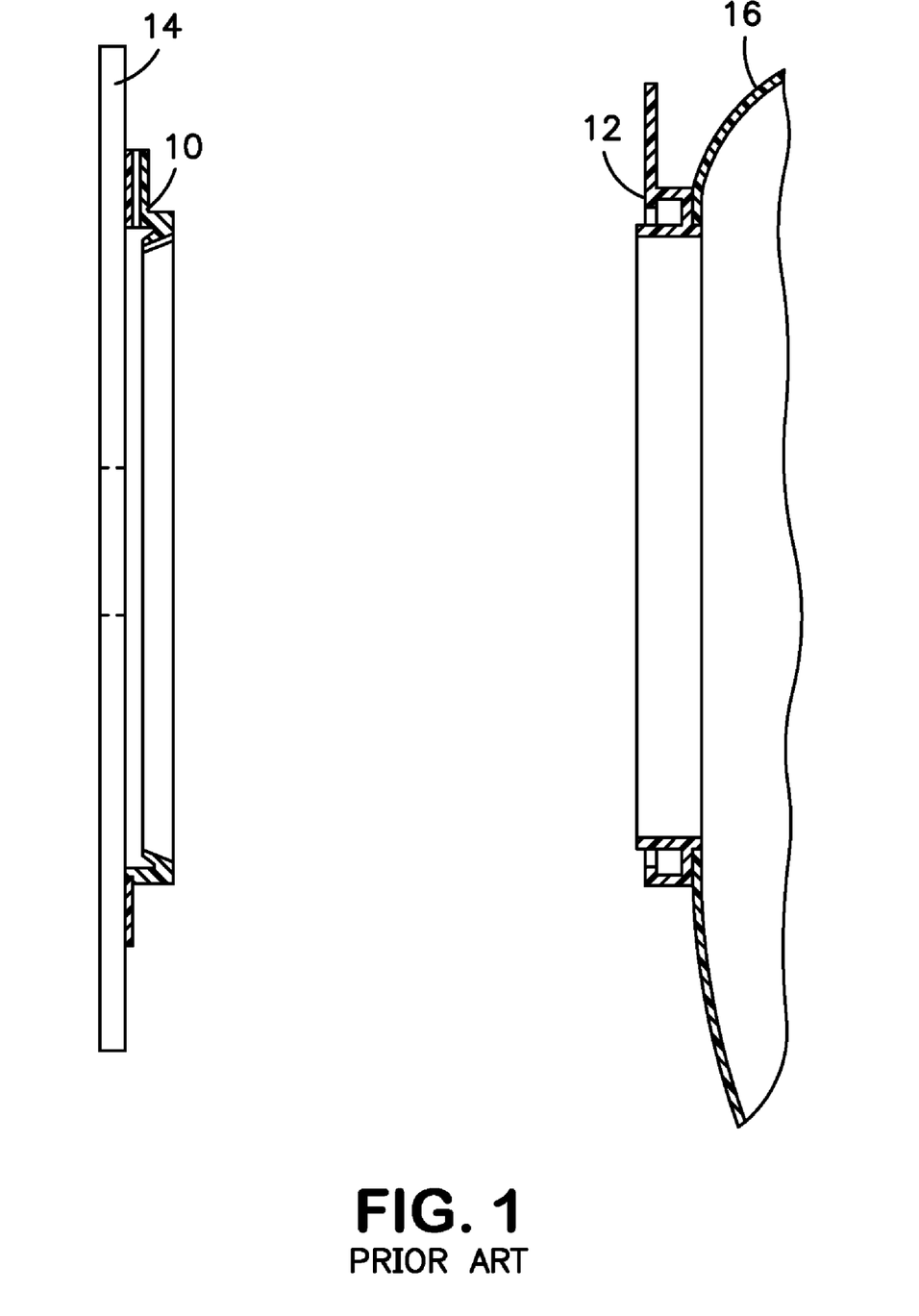
FIG. 1 is a schematic sectional view of a prior art ostomy coupling according to GB 1571657.

The ostomy coupling shown in British Patent Specification No. 1571657 and illustrated in FIG. 1 of the present application has received wide acceptance and approval among ostomates. The coupling comprises first and second inter-engageable coupling parts 10, 12 which are securable together with a press fit. The first coupling part 10 comprises an annular rib and is directly mounted on an adhesive wafer 14 of the body fitment. The second coupling part 12 comprises an annular channel member and is mounted around the mouth of a collection pouch 16. The coupling parts 10, 12 are manufactured in a range of different diameters to suit different stoma size requirements, and the ostomate selects components of matching coupling size.

U.S. Pat. No. 4,419,100, U.S. Pat. No. 4,610,676, U.S. Pat. No. 4,610,677 and U.S. Pat. No. 5,730,735 teach a modification designed to reduce discomfort that some ostomates may experience as a result of the attachment force applied through the body fitment to the skin, when the coupling parts are pressed together. The problem of discomfort is especially important during post-operative care, when the stoma surgery is recent and the abdominal skin is very tender. These latter documents teach a flexible collar suspension permanently secured between the adhesive wafer and the coupling part of the body fitment. The flexible collar allows the coupling part to be displaced away from or "float" with respect to the adhesive wafer, at least by a sufficient amount for a user to insert one or more fingers behind the coupling part, in order to manually support the coupling part against the attachment force when the appliance is pressed against the body fitment. While this technique is successful in reducing transmission of the attachment force to the sensitive abdominal skin during post-operative care, there are several disadvantages that make this type of coupling less than ideal for everyday use: (1) the appliances tend to be larger than equivalent systems where no flexible collar is used; (2) the profile of the system is higher than similar systems without a flexible collar, due to the increased thickness; (3) there is a tendency for the appliance to sag away from the adhesive wafer, since the flexible collar is explicitly provided to allow the pouch to float away from the surface of the wafer; and (4) the cost of the device is higher than a conventional system without a flexible collar, since the manufacturing costs are higher. A manufacturer wishing to accommodate specific customer preferences for post-operative care, and also different customer preferences for everyday use, would need to manufacture different types of body fitment both with, and without, the flexible collar, leading to significant burden of increased inventory and manufacturing costs.

The present invention has been devised bearing the above in mind.

SUMMARY OF THE INVENTION

In one form, the present invention provides an adapter for an ostomy coupling. The adapter provides a floatable coupling characteristic, for an ostomy body fitment that has a non-floatable coupling part.

Thus, the invention solves the problem of increased inventory and manufacturing costs by enabling a single type of body fitment, with a non-floatable coupling part, equally to be used with the adapter to provide a floatable characteristic. Use of such an adapter can avoid the need for a manufacturer to produce, and stock, different types of body fitment with, and without, the floatable coupling feature. Instead, when a floatable coupling part is desired for post-operative or specialized care, the ostomate or care giver can use a standard body fitment without a floatable coupling part, and attach the adapter to that body fitment to obtain the desired floatable coupling feature. The adapter can thereby significantly enhance the versatility of existing ostomy equipment, and reduce inventory and manufacturing cost burden to meet different ostomates' preferences.

The adapter comprises a first coupling part for attaching to the body fitment, a second coupling part for releasably attaching to an ostomy appliance, and a flexible collar between the first and second coupling parts. The flexible collar permits the second coupling part to be displaced away from the first coupling part, thereby creating a space for an ostomate to manually brace the second coupling part against an attachment force when an appliance is fitted.

As used herein, the term "releasably attaching" and derivatives thereof mean that two coupling parts are attachable and detachable, using forces applied by hand, and without destruction of either part. The term "floatable" means that a coupling part is movable towards and away from an adhesive wafer, to create a space for a user to manually brace that coupling part, in order to relieve attachment forces being applied through the adhesive wafer.

While features believed to be most important are highlighted above, in description, and in the appended claims, the Applicants may seek claims protection for any novel feature or idea disclosed herein and/or in the drawings, whether or not emphasis has been placed thereon.

DETAILED DESCRIPTION OF PREFERRED EMBODIMENTS

In the accompanying drawings, the same reference numerals are used to denote the same or equivalent features in each embodiment.

Figure 2:
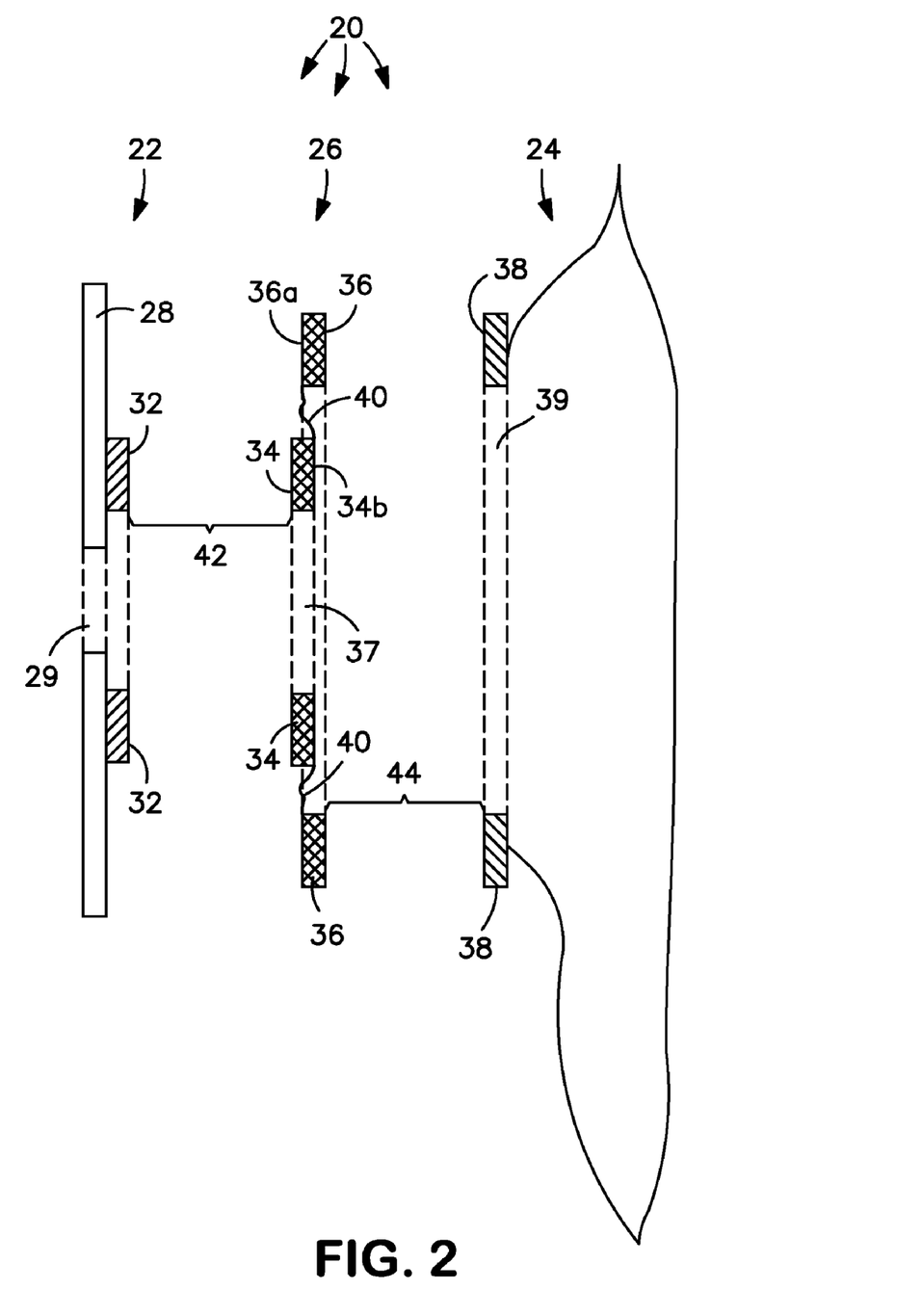
FIG. 2 is a schematic exploded sectional view showing elements of an ostomy appliance of a first embodiment using an adapter of the present invention.
Figure 3:
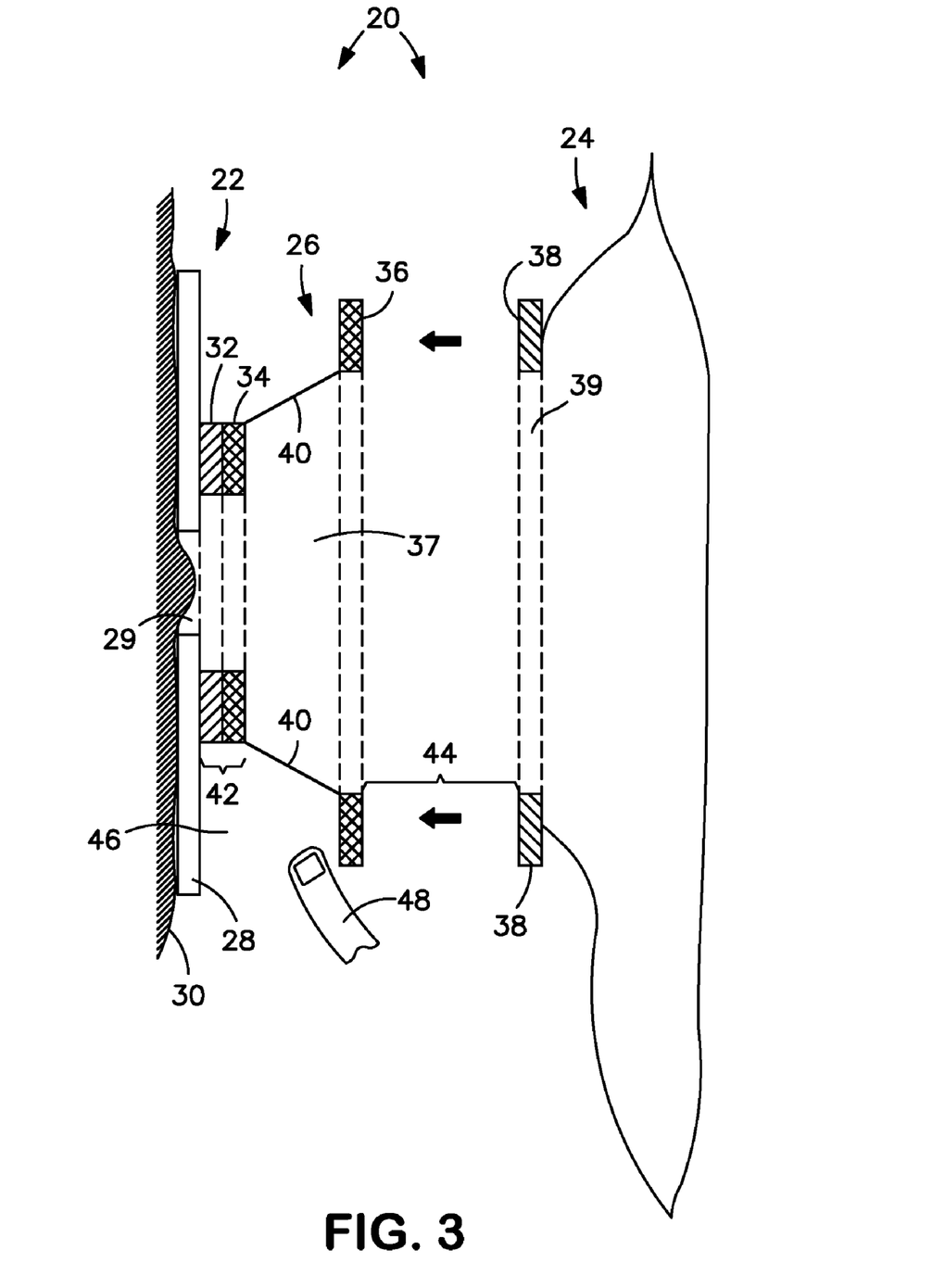
FIG. 3 is a schematic sectional view similar to FIG. 2, showing the ostomy appliance in use.

Referring to FIGS. 2 and 3, ostomy apparatus 20 generally comprises a body fitment 22, an ostomy appliance 24, and an adapter 26. The body fitment 22 comprises an adhesive wafer 28 with a stomal orifice 29, for attachment to the ostomate's skin 30 (FIG. 3), and a body fitment coupling part 32 that is secured to the adhesive wafer 28 around the stomal orifice 29. The adhesive wafer 28 may be made of any suitable skin-friendly ostomy adhesive, such as described in U.S. Pat. No. 4,166,051, U.S. Pat. No. 4,393,080, or other compositions designed for use around a stoma. The body fitment coupling part 32 is secured in such a manner that at least a portion of the coupling part 32 is fixed in position with respect to the wafer 28. For example, the body fitment coupling part 32 may be welded or bonded to the adhesive wafer 28 or a backing (not shown) of the adhesive wafer 28. The body fitment coupling part 32 may be referred to as non-floatable, since it is not possible to displace the body fitment coupling part 32 substantially with respect to the adhesive wafer 28.

The ostomy appliance 24 comprises a collection pouch, although the invention is applicable to any form of ostomy appliance, such as a stoma port, or a controlled discharge appliance. The ostomy appliance 24 also comprises an appliance coupling part 38 surrounding an entrance aperture 39 of the ostomy appliance 24.

The adapter 26 serves to provide the body fitment 22 with a floatable coupling part characteristic. By using the adapter 26, the manufacturing and inventory burden can be significantly reduced, because the adapter 26 can avoid the need for a manufacturer to produce, and stock, different types of body fitment 22 with, and without, the floatable coupling feature. Instead, when a floatable coupling part is desired for post-operative or specialized care, the ostomate or care giver can use a standard body fitment 22 without a floatable coupling part, and attach the adapter 26 to that body fitment 22 to obtain the desired floatable coupling feature.

The adapter 26 comprises a first coupling part 34 for attaching to the body-fitment coupling part 32, as a first ostomy coupling 42. The adapter 26 further comprises a second coupling part 36 for releasable attachment to the appliance coupling part 38, as a second ostomy coupling 44. The adapter 26 further comprises a flexible collar 40 for permitting the second coupling part 36 to move, or "float" with respect to the first coupling part 34. The flexible collar 40 extends at least partly between the first and second coupling parts 34, 36. The flexible collar 40, and the first and second coupling parts 34, 36 generally have a closed loop shape, such as round annular or tubular, around a through passage 37 for a stoma or stomal effluent.

In the present embodiment, the flexible collar 40 is a separate member that is permanently secured to the first and second coupling parts 34, 36 by any suitable manner, such as welding or adhesive bonding. However, the flexible collar 40 could be integrally molded with one or both of the first and second coupling parts 34, 36, if desired.

The flexible collar 40 may have any suitable form such as comprising one or more of: stretchable material; foamed material, flat sheet material; flexible film; and/or material formed with accordion folds.

The coupling parts 34, 36, 38 are depicted schematically in FIGS. 2 and 3 by blocks. However, it will be appreciated that the coupling parts 34, 36, 38 may have different shapes, such as thin, or three-dimensional profiles. The first and second couplings 42, 44 may both be of a mechanical type, using mechanical interlock or interference to secure the respective coupling parts together. The later embodiments illustrate a mechanical coupling in which mutual interlock or interference is produced between the coupling parts 34, 36, 38. Alternatively, the first and second couplings 42, 44 may both be of an adhesive type, in which one or both of the confronting coupling parts 34, 36, 38 carries an adhesive for adhering to the complementary confronting part. The other confronting part may also be adhesive, or it may be a planar non-adhesive landing surface for engaging the adhesive coupling part. Alternatively, one of the first and second couplings 42, 44 may be of an adhesive type, and the other may be of a mechanical type.

The first coupling part 34 may optionally be of an equivalent coupling type to the appliance coupling part 38 (except that the sizes of the coupling parts may be different). The second coupling part 36 may optionally be of an equivalent coupling type to the body fitment coupling part 32 (except that the sizes of the coupling parts may be different).

At least the second coupling 44 is of a releasably attachable type to permit fitting, detachment and renewal of an ostomy appliance 24. The first coupling 42 may also be of a releasably attachable type in order to allow the adapter 26 to be removed from the body fitment 22 after first fitting, e.g., to facilitate cleaning or to enable the same adapter 26 to be used multiple times with different body fitments 22. Alternatively, the first ostomy coupling 42 may be of a type that is non-releasable (or at least less-easily releasable) in order to prevent accidental detachment of the adapter 26 after it is first fitted to the body fitment 22. For example, when the first ostomy coupling 42 is of an adhesive type, it is preferred that the first ostomy coupling 42 be a releasably attachable coupling, for example, comprising a peelable-resealable adhesive, such as an acrylate-based peelable-resealable adhesive. When the first ostomy coupling 42 is of a mechanical type, the first ostomy coupling 42 may be a releasably attachable coupling, or a non-releasably attachable coupling.

In use, the adapter 26 is first attached to the body fitment 22 by means of the first ostomy coupling 42. It is preferred that the adapter 26 be attached to the body fitment 22 before the body fitment 22 is then attached to the body, in order to avoid the attachment force when fitting the adapter 26 causing any discomfort to the ostomate. However, the adapter 26 is versatile enough to be fitted to the body fitment 22 while the body fitment 22 is already adhered to the body, if so desired.

Referring to FIG. 3, in order to attach the ostomy appliance 24, the ostomate displaces the second coupling part 36 in a direction away from the body fitment 22, in order to provide space 46 between the second coupling part 36 and the body fitment 22 for the ostomate to insert one or more fingers 48 of one or both hands. Although only one finger 48 is shown at one position in FIG. 3, it will be appreciated that the ostomate may insert his fingers at several points to brace the second coupling part 36 around its periphery. Then, using the fingers 48 to brace the second coupling part 36 against the attachment force, the ostomate presses appliance coupling part 38 into engagement with the second coupling part 36, in order to secure the ostomy appliance 24 to the adapter 26. The ostomate then removes the fingers 48, allowing the second coupling part 34 to return towards the body fitment 22.

The transverse dimension (e.g., diameter) of the second coupling part 36 is generally not less than that of the first coupling part 34. In the illustrated form, the second coupling part 36 has a larger internal dimension (e.g. internal diameter) than the outer dimension (e.g. outer diameter) of the first coupling part 34. This permits the second coupling part 36 to fit at least partly around the first coupling part 34, such that the adapter 26 can adopt a generally planar, low profile configuration, if desired. Referring to FIG. 2, in the generally planar configuration, the rear 36a of the second coupling part 36 may be not substantially further from the surface of the adhesive wafer 28 than is the front 34b of the first coupling part 34. In a preferred form, the rear 36a of the second coupling part may be closer to the surface of the adhesive wafer 28 than is the front 34a of the first coupling part 34, such that the two coupling parts 34, 36 partly overlap. In an even more preferred form, the rear 36a of the second coupling part 36 may touch the adhesive wafer 28 (or is backing). The profile height of the body fitment 22 with the adapter 26 can be generally the same as, or not significantly greater than, that of the body fitment 22 alone.

The first and second coupling parts 34, 36 can be selected so as to match different sizes from a manufacturer's existing range of coupling sizes. For example: the first coupling part 34 may be a 45 mm diameter size, to fit a body fitment with a 45 mm coupling part; the second coupling part 36 may be a 57 mm diameter size, to fit an appliance with a 57 mm coupling part. Although the size of the appliance coupling part 38 does not match the size of the body fitment coupling part 32, the two sizes may nevertheless be selected from the range of standard sizes of a manufacturer's existing range of products, so that no extra manufacturing burden is placed on the manufacturer.

In an alternative modification (described later with respect to FIGS. 9 and 10), the first and second coupling parts 34, 36 may be of substantially the same coupling size, such that the coupling parts 34, 36 sit back to back. Such a design might not provide for the same degree of low profile as the nested design of FIGS. 2 and 3, but may enable the adapter 26 to be used as an option between a body fitment 22 and an ostomy appliance 24 having matching coupling sizes.

The adapter 26 may be used with a single body fitment 22. For example, the adapter 26 may have a rated life equivalent to that of the body fitment 22. Alternatively, the adapter 26 may be intended to be used multiple times with different body fitments 22. The adapter 26 may be configured to withstand a greater number of "flexes" of the flexible collar 40 without plastic deformation, and to withstand cleaning between different uses.

A range of different adapters 26 may be provided, for example, having different throw lengths and/or different stiffnesses of the flexible collar 40. This may further enhance the versatility that the adapter 26 can provide to a standard body fitment 22.

Figure 4:
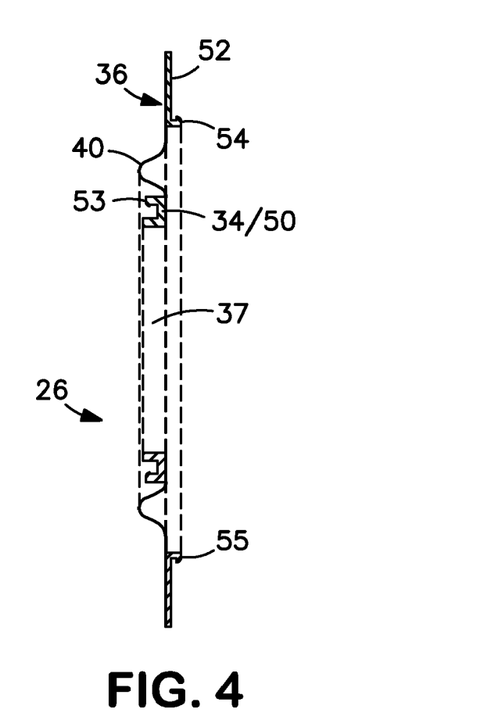
FIG. 4 is a schematic sectional view showing an adapter of a second embodiment in a generally planar condition.
Figure 5:
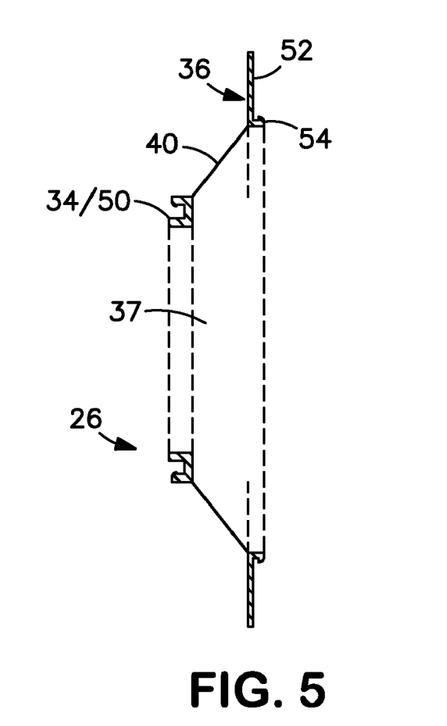
FIG. 5 is a schematic sectional view showing the adapter of the second embodiment in a distended condition.

FIGS. 4 and 5 illustrate in more detail a second embodiment of the adapter 26. In the second embodiment, the first coupling part 34 comprises an annular channel 50 for forming an interlocking press-fit with a complementary annular rib (not shown) of the body fitment coupling part 32. The annular channel 50 may include one or more undercut projections 53 for forming the interlocking engagement, in a similar manner to that described in the aforementioned GB-A-1571657. The second coupling part 36 comprises a radially projecting flange 52 from which projects an annular rib 54 for forming an interlocking press-fit with a complementary annular channel of the appliance coupling part 38. The annular rib 54 may include an undercut projection 55 for forming the interlock and/or a sealing wiper (not shown), both as described in GB-A-1571657. The flange 52 acts as: (i) a finger grip for allowing an ostomate to displace the second coupling part 36 axially away from the first coupling part 34 (as in FIG. 5), in order to generate the space 46; and (ii) as a wall behind which the ostomate's fingers 48 can locate to brace the second coupling part 36 against the attachment force. The coupling parts 34, 36 are molded from plastics material that is stiffly flexible, having a self-supporting shape.

The flexible collar 40 comprises a plastics film, such as ethylene-vinyl acetate, with a thickness of about 0.25 mm. The plastics film is molded or formed in a cone shape as illustrated in FIG. 5 to suit the distended shape of the flexible collar 40, and may collapse into a folded shape as illustrated in FIG. 4, when the flexible collar 40 is collapsed. The plastics film may have bistable properties, such that the flexible collar 40 tends to return to either of the shapes of FIGS. 4 and 5, as is described in more detail in our concurrently filed PCT application derived from U.S. Provisional Application Nos. 60/968,403 and 60/956,238. The flexible collar 40 may be secured to the first and second coupling parts 34, 36 by, for example, welding or adhesive bonding.

Figure 6:
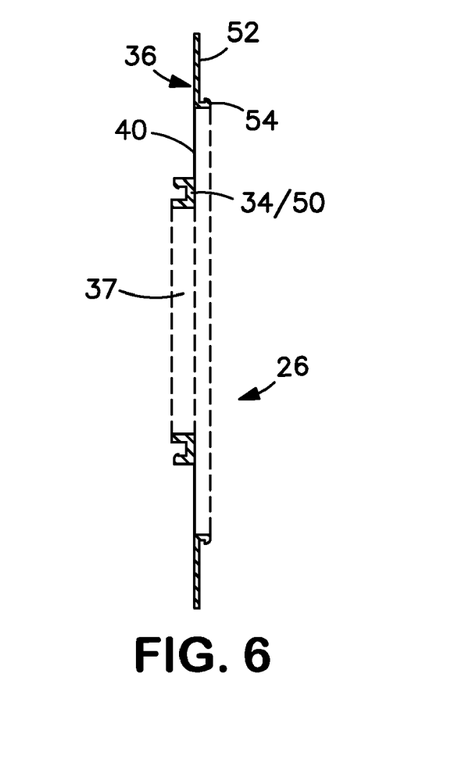
FIG. 6 is a schematic sectional view showing an adapter of a third embodiment.

FIG. 6 illustrates a third embodiment of the adapter 26 similar to the second embodiment. The main difference is that the film of the flexible collar 40 is formed in a generally planar shape. The flexibility of the film allows the second coupling part 36 to be displaced forward of the first coupling part 34, to create the space 46 for the user's fingers. The film may be resiliently stretchable, or it may be non-stretchable.

Figure 7:
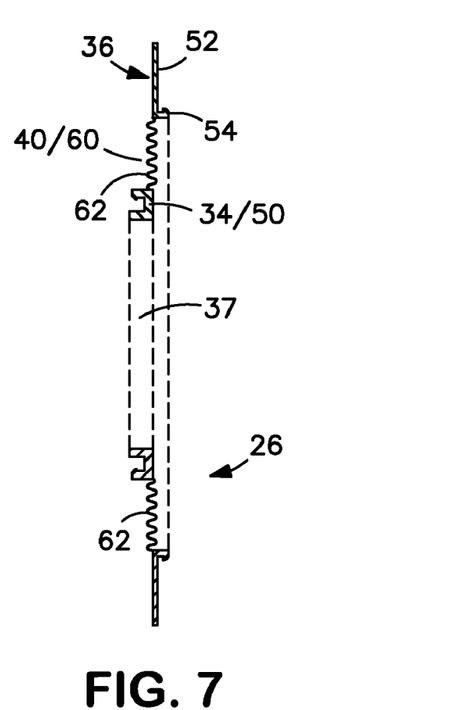
FIG. 7 is a schematic sectional view showing an adapter of a fourth embodiment in a generally planar condition.
Figure 8:
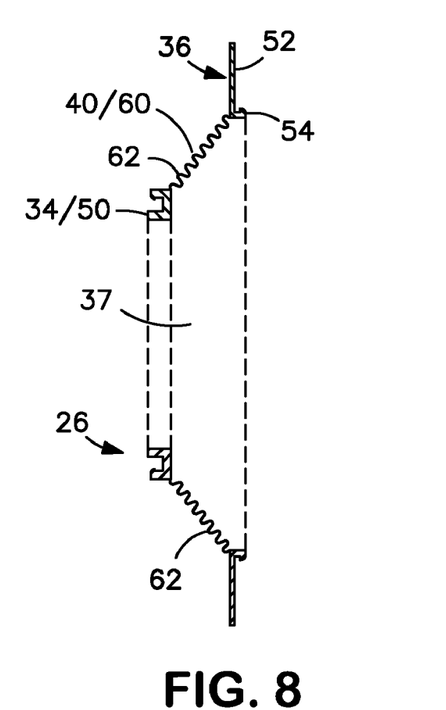
FIG. 8 is a schematic sectional view showing the adapter of the fourth embodiment in a distended condition.

FIGS. 7 and 8 illustrate a fourth embodiment of the adapter 26 similar to the second embodiment. The main difference is that the flexible collar 40 comprises a molded plastics member 60, with accordion folds 62 to make the flexible collar 40 more supple and permit the flexible collar 40 to distend to a cone shape (FIG. 8). The plastics member 60 may be molded in a generally planar shape (FIG. 7), and be resiliently deformable to the distended cone shape (FIG. 8). A suitable plastics is a polyethylene blend and the member may have a thickness of about 0.25 mm. The plastics member 60 may be a separate piece that is secured to the first and second coupling parts 34, 36 by, for example, welding or bonding. Alternatively, the plastics member 60 may be integrally molded with one or both of the first and second coupling parts 34, 36.

Figure 9:
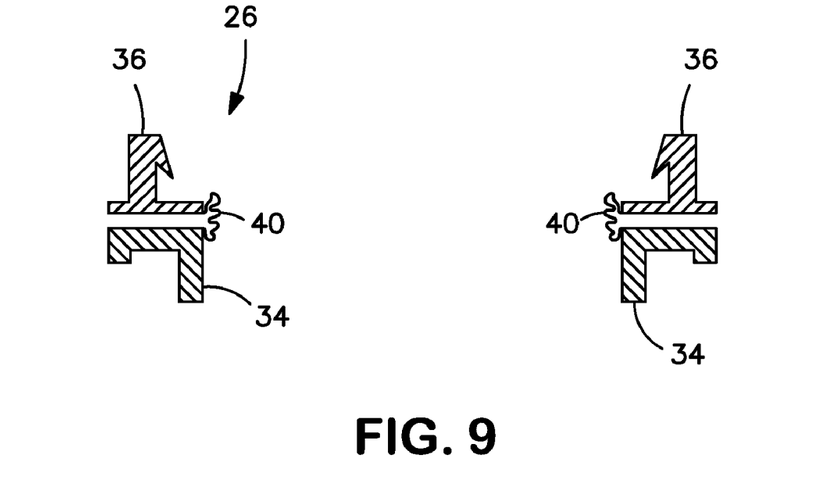
FIG. 9 is a schematic sectional view showing an adapter of a fifth embodiment in a retracted condition.
Figure 10:
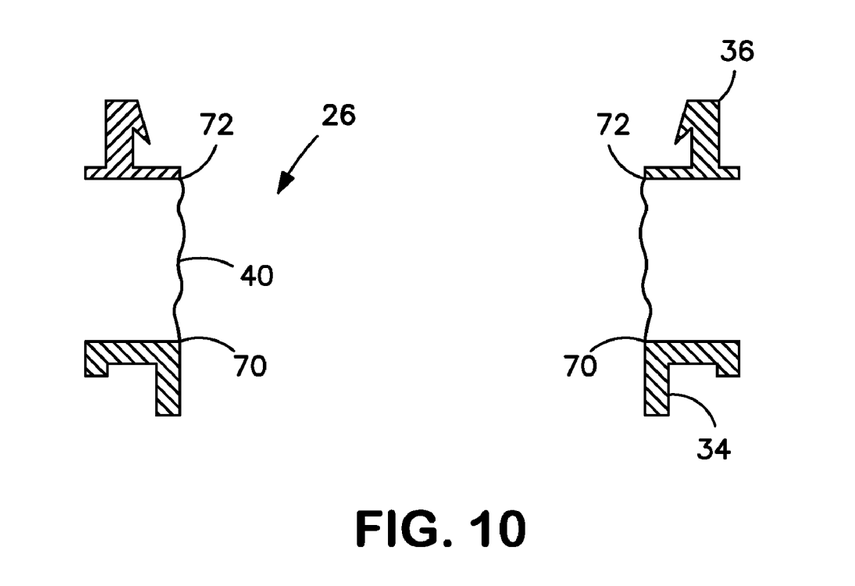
FIG. 10 is a schematic sectional view showing the adapter of the fifth embodiment in a distended condition.

FIGS. 9 and 10 illustrate a fifth embodiment similar to the preceding embodiments except that, in the fifth embodiment, the flexible support collar 40 extends between coupling parts of substantially the same diameter. The flexible support collar 40 comprises a first end 70 secured to the first coupling part 34, and a second end 72 secured to the second coupling part 36. The first and second ends 70, 72 are of substantially the same diameter, thereby enabling the adapter 26 to fit between a body fitment 22 and an ostomy appliance 24 having coupling parts of matching size. This is advantageous by providing fully compliant modularity, using existing ostomy components of matching size. A user can choose selectively whether to attach the ostomy appliance 24 directly to the body fitment 22, or whether to employ the adapter 26 (for example, for post-operative or other special care when the stoma is particularly sensitive).

The flexible support collar 40 of the fifth embodiment can take a variety of forms. In one form as illustrated, the flexible support collar 40 is generally tubular, forming an extended tube when in the extended condition (FIG. 10), and a concertina-folded O-ring when in the retracted condition (FIG. 19). The flexible support collar 40 may be molded in one condition (such as the retracted condition), and be extendable to the other position. Other possible shapes and forms of the flexible support collar 40 are possible, such as folding and/or stretchable, referring to the possibilities aforementioned. Optionally, the flexible support collar 40 may have bistable properties, as is described in more detail in our concurrently filed PCT application derived from U.S. Provisional Application Nos. 60/968,403 and 60/956,238.

The flexible support 40 is shaped so that, in the retracted position, the flexible support collar 40 does not substantially obstruct back-to-back positioning of the coupling parts 34 and 36 of the adapter 26 (see FIG. 9). This permits the adapter 26 to adopt a low-profile shape in the retracted condition, so as limit the extent to which the adapter 26 adds to the profile of the ostomy appliance 24 and the body fitment 22 in use. It will be appreciated that the ends of the tubular support collar 40 may be attached to the back-to-back faces of the coupling parts 34, 36, but this does not significantly space the coupling parts 34, 36 from each other in the retracted position.

It will be appreciated that modifications, improvements and equivalents may fall within the scope of the invention as claimed.

We claim:

1. An adapter for an ostomy coupling, the adapter being configured to fit between a body fitment coupling part of a body fitment and an appliance coupling part of an ostomy appliance, the adapter comprising:
   a first coupling part configured for attaching to the body fitment coupling part;
   a second coupling part configured for releasably attaching to the appliance coupling part; and
   a flexible collar between the first and second coupling parts, the flexible collar permitting the second coupling part to be displaced away from the first coupling part, to provide a space for a user manually to brace the second coupling part when fitting the ostomy appliance wherein the body fitment with adapter attached has a profile height not significantly greater than that of the body fitment alone.

2. The adapter according to claim 1, wherein the adapter has a through passage, and the first and second coupling parts and the flexible collar each extend around the through passage.

3. The adapter according to claim 1, wherein at least one of the first and second coupling parts comprises a mechanical interlock profile.

4. The adapter according to claim 3, wherein the mechanical interlock profile is selected from: a channel; and a rib.

5. The adapter according to claim 4, wherein the one of first and second coupling parts comprises a channel and the other comprises a rib.

6. The adapter according to claim 1, wherein at least one of the first and second coupling parts comprises an adhesive coupling part.

7. The adapter according to claim 1, wherein at least one of the first and second coupling parts comprises a generally planar non-adhesive landing surface for engaging a complementary adhesive coupling part.

8. The adapter according to claim 1, wherein the flexible collar comprises stretchable material.

9. The adapter according to claim 1, wherein the flexible collar comprises foamed material.

10. The adapter according to claim 1, wherein the flexible collar comprises substantially flat material.

11. The adapter according to claim 1, wherein the flexible collar comprises flexible film material.

12. The adapter according to claim 1, wherein the flexible collar is formed with accordion folds.

13. The adapter according to claim 1, wherein the first and second coupling parts have different orifice dimensions.

14. The adapter according to claim 1, wherein the internal dimension of the second coupling part is not smaller than the external dimension of the first coupling part.

15. The adapter according to claim 1, wherein the first and second coupling parts are of substantially the same coupling size.

16. The adapter according to claim 1, wherein the first and second coupling parts and the flexible collar are formed as one unit.

17. The adapter according to claim 1, wherein the first and second coupling parts are formed as one unit and the flexible collar is a separate unit.

18. The adapter according to claim 1, wherein the first coupling part and the flexible collar are formed as one unit and the second coupling part is a separate unit.

19. The adapter according to claim 1, wherein the second coupling part and the flexible collar are formed as one unit and the first coupling part is a separate unit.

20. An ostomy apparatus comprising:
   a body fitment comprising an adhesive wafer for attachment to the skin, and
   a body fitment coupling part, the body fitment coupling part including a stomal orifice; and
   an adapter for coupling to the body fitment, the adapter including a first coupling part for attaching to the body fitment coupling part, a second coupling part for releasably attaching to an ostomy appliance, and a flexible collar between the first and second coupling parts, the adapter having a through passage around which the first and second coupling parts and the flexible collar each extend, and the flexible collar permitting, in use, an ostomate to displace the second coupling part to create a space between the second coupling part and the body fitment to manually brace the second coupling part against an attachment force when attaching the appliance to the second coupling part wherein the body fitment with adapter attached has a profile height not significantly greater than that of the body fitment alone.

21. The apparatus according to claim 20, wherein at least a portion of the body fitment coupling part is substantially fixed in position with respect to the adhesive wafer.

22. The apparatus according to claim 20, further comprising an ostomy appliance having an appliance coupling part extending around an entrance aperture, wherein the second coupling part is configured for releasable attachment to the appliance coupling part.

23. A method comprising:
   providing a body fitment having a non-floatable body fitment coupling part;
   providing an adapter comprising a first coupling part, a second coupling part, and a flexible collar between the first and second coupling parts; and
   attaching the first coupling part of the adapter to the non-floatable body fitment coupling part, in order to provide a floatable coupling part characteristic for the body fitment wherein the body fitment with adapter attached has a profile height not significantly greater than that of the body fitment alone.

24. Use of an adapter to provide a floatable coupling characteristic for a body fitment that has a non-floatable body fitment coupling part, the adapter comprising:
   a first coupling part for attaching to the non-floatable body fitment coupling part;
   a second coupling part for releasably attaching to an ostomy appliance; and
   a flexible collar between the first and second coupling parts, the flexible collar permitting displacement of the second coupling part with respect to the first coupling part wherein the body fitment with adapter attached has a profile height not significantly greater than that of the body fitment alone.

* * * * *